(12) United States Patent
Poker et al.

(10) Patent No.: US 10,449,335 B2
(45) Date of Patent: Oct. 22, 2019

(54) PEELABLE PROTECTIVE SHEATH

(71) Applicant: C. R. Bard, Inc., Murray Hill, NJ (US)

(72) Inventors: Rachel Poker, San Francisco, CA (US); Bruce Asmus, Hopkins, MN (US)

(73) Assignee: C.R. Bard, Inc., Murray Hill, NJ (US)

( * ) Notice: Subject to any disclaimer, the term of this patent is extended or adjusted under 35 U.S.C. 154(b) by 36 days.

(21) Appl. No.: 14/888,378

(22) PCT Filed: May 2, 2014

(86) PCT No.: PCT/US2014/036693
§ 371 (c)(1),
(2) Date: Oct. 30, 2015

(87) PCT Pub. No.: WO2014/179767
PCT Pub. Date: Nov. 6, 2014

(65) Prior Publication Data
US 2016/0058983 A1    Mar. 3, 2016

Related U.S. Application Data

(60) Provisional application No. 61/819,433, filed on May 3, 2013.

(51) Int. Cl.
*A61M 25/10* (2013.01)
*B29C 48/10* (2019.01)
(Continued)

(52) U.S. Cl.
CPC .......... *A61M 25/1002* (2013.01); *A61L 29/06* (2013.01); *A61L 29/08* (2013.01);
(Continued)

(58) Field of Classification Search
CPC ...... A61M 2025/1081; A61M 25/0668; A61M 25/10; A61M 25/1002; A61M 25/1029;
(Continued)

(56) References Cited

U.S. PATENT DOCUMENTS 4,306,562 A * 12/1981 Osborne ........... A61M 25/0668
604/164.05
4,473,067 A    9/1984 Schiff
(Continued)

FOREIGN PATENT DOCUMENTS

JP    2000-516502 A    12/2000
JP    2005-211492 A    8/2005
(Continued)

OTHER PUBLICATIONS

Definition of Texture (Dictionary.com on Apr. 9, 2018).*
(Continued)

*Primary Examiner* — Laura A Bouchelle
*Assistant Examiner* — Dung T Ulsh
(74) *Attorney, Agent, or Firm* — Rutan & Tucker, LLP

(57) ABSTRACT

A peelable protective sheath and related assemblies/systems and methods are disclosed. The protective sheath may be used on a balloon catheter to protect the balloon and any coating thereon. The protective sheath may be peelable to make removal of the protective sheath easier. The peelable protective sheath may be inserted into a hemostatic valve and introducer while still disposed over the balloon of a balloon catheter to protect the balloon and any bioactive coating thereon from damage during insertion. The peelable protective sheath may be peeled from a proximal end to initiate removal. Alternatively, the peelable protective sheath may be peeled from a distal end of the peelable protective sheath as the balloon catheter is inserted through a hemostatic valve and introducer.

34 Claims, 4 Drawing Sheets

(51) Int. Cl.
*B29C 48/00* (2019.01)
*A61L 29/06* (2006.01)
*A61L 29/08* (2006.01)
*A61L 29/16* (2006.01)
*A61F 2/958* (2013.01)
*A61F 2/97* (2013.01)
*B29K 27/18* (2006.01)
*B29K 31/00* (2006.01)
*B29L 31/00* (2006.01)

(52) U.S. Cl.
CPC ............ *A61L 29/16* (2013.01); *A61M 25/10* (2013.01); *A61M 25/104* (2013.01); *A61M 25/1029* (2013.01); *A61M 25/1036* (2013.01); *B29C 48/0019* (2019.02); *B29C 48/0022* (2019.02); *B29C 48/10* (2019.02); *A61F 2/958* (2013.01); *A61F 2/97* (2013.01); *A61L 2300/606* (2013.01); *A61M 2025/1004* (2013.01); *A61M 2025/105* (2013.01); *A61M 2025/1081* (2013.01); *B29K 2027/18* (2013.01); *B29K 2995/0098* (2013.01); *B29L 2031/7543* (2013.01)

(58) Field of Classification Search
CPC ............ A61M 25/1036; A61M 25/104; A61M 2025/1004; A61M 2025/105; A61M 2025/0675; A61F 2/958; A61F 2/97
See application file for complete search history.

(56) References Cited

U.S. PATENT DOCUMENTS

| | | | |
|---|---|---|---|
| 4,649,922 A | 3/1987 | Wiktor | |
| 4,921,479 A | 5/1990 | Grayzel | |
| 5,015,231 A | 5/1991 | Keith et al. | |
| 5,125,904 A * | 6/1992 | Lee | A61M 25/0668 604/161 |
| 5,147,302 A | 9/1992 | Euteneuer et al. | |
| 5,158,545 A * | 10/1992 | Trudell | A61F 2/90 604/104 |
| 5,167,634 A * | 12/1992 | Corrigan, Jr. | A61M 25/0668 604/160 |
| 5,176,698 A | 1/1993 | Burns et al. | |
| 5,211,654 A | 5/1993 | Kaltenbach | |
| 5,221,263 A | 6/1993 | Sinko et al. | |
| 5,222,970 A | 6/1993 | Reeves | |
| 5,342,307 A | 8/1994 | Euteneuer et al. | |
| 5,352,236 A | 10/1994 | Jung et al. | |
| 5,366,442 A | 11/1994 | Wang et al. | |
| 5,425,710 A | 6/1995 | Khair et al. | |
| 5,445,645 A | 8/1995 | Debbas | |
| 5,454,790 A * | 10/1995 | Dubrul | A61M 25/0668 604/104 |
| 5,458,639 A | 10/1995 | Tsukashima et al. | |
| 5,484,409 A | 1/1996 | Atkinson et al. | |
| 5,496,345 A * | 3/1996 | Kieturakis | A61B 17/0218 600/204 |
| 5,499,975 A * | 3/1996 | Cope | A61M 25/0662 604/164.1 |
| 5,522,818 A | 6/1996 | Keith et al. | |
| 5,569,294 A | 10/1996 | Parkola | |
| 5,584,852 A | 12/1996 | Parkola | |
| 5,591,226 A * | 1/1997 | Trerotola | A61B 17/11 606/108 |
| 5,647,857 A | 7/1997 | Anderson et al. | |
| 5,702,410 A | 12/1997 | Klunder et al. | |
| 5,765,682 A | 6/1998 | Bley et al. | |
| 5,766,203 A * | 6/1998 | Imran | A61F 2/958 604/103.05 |
| 5,800,517 A | 9/1998 | Anderson et al. | |
| 5,824,041 A | 10/1998 | Lenker et al. | |
| 5,868,707 A * | 2/1999 | Williams | A61M 25/10 604/103 |
| 5,868,719 A | 2/1999 | Tsukernik | |
| 5,873,880 A | 2/1999 | Williams et al. | |
| 5,893,868 A * | 4/1999 | Hanson | A61F 2/0095 606/192 |
| 5,964,730 A | 10/1999 | Williams et al. | |
| 6,110,146 A * | 8/2000 | Berthiaume | A61M 25/09041 604/103 |
| 6,113,607 A | 9/2000 | Lau et al. | |
| 6,132,450 A | 10/2000 | Hanson et al. | |
| 6,143,016 A * | 11/2000 | Bleam | A61F 2/958 604/104 |
| 6,152,944 A | 11/2000 | Holman et al. | |
| 6,251,119 B1 * | 6/2001 | Addis | A61B 17/3415 128/898 |
| 6,283,743 B1 | 9/2001 | Traxler et al. | |
| 6,416,529 B1 | 7/2002 | Holman et al. | |
| 6,432,121 B1 * | 8/2002 | Jervis | A61B 17/00234 606/190 |
| 6,447,540 B1 | 9/2002 | Fontaine et al. | |
| 6,454,744 B1 | 9/2002 | Spohn et al. | |
| 6,530,881 B1 * | 3/2003 | Ailinger | A61B 1/00142 600/114 |
| 6,533,806 B1 | 3/2003 | Sullivan et al. | |
| 6,562,049 B1 * | 5/2003 | Norlander | A61M 25/003 606/108 |
| 6,569,182 B1 | 5/2003 | Balceta et al. | |
| 6,592,602 B1 * | 7/2003 | Peartree | A61B 17/00234 600/204 |
| 6,613,067 B1 | 9/2003 | Johnson | |
| 6,663,595 B2 | 12/2003 | Spohn et al. | |
| 6,749,584 B2 | 6/2004 | Briggs et al. | |
| 6,749,601 B2 | 6/2004 | Chin | |
| 6,758,854 B1 * | 7/2004 | Butler | A61M 25/0041 604/101.01 |
| 6,783,542 B2 | 8/2004 | Eidenschink | |
| 6,790,224 B2 | 9/2004 | Gerberding | |
| 6,899,727 B2 | 5/2005 | Armstrong et al. | |
| 6,939,327 B2 | 9/2005 | Hall et al. | |
| 6,991,639 B2 | 1/2006 | Holman et al. | |
| 7,105,013 B2 | 9/2006 | Durcan | |
| 7,144,386 B2 | 12/2006 | Korkor et al. | |
| 7,198,636 B2 | 4/2007 | Cully et al. | |
| 7,468,070 B2 | 12/2008 | Henry et al. | |
| 7,497,844 B2 | 3/2009 | Spear et al. | |
| 7,618,398 B2 | 11/2009 | Holman et al. | |
| 7,632,256 B2 | 12/2009 | Mosler et al. | |
| 7,744,571 B2 | 6/2010 | Fisher et al. | |
| 7,770,726 B2 | 8/2010 | Murray et al. | |
| 7,837,671 B2 | 11/2010 | Eversull et al. | |
| 7,909,798 B2 | 3/2011 | Osypka | |
| 7,967,798 B2 | 6/2011 | Reydel et al. | |
| 7,993,305 B2 | 8/2011 | Ye et al. | |
| 7,998,184 B2 | 8/2011 | Eidenschink | |
| 8,025,691 B2 | 9/2011 | Carter et al. | |
| 8,105,287 B2 | 1/2012 | Fisher et al. | |
| 8,126,570 B2 | 2/2012 | Manning et al. | |
| 8,202,309 B2 | 6/2012 | Styrc | |
| 8,273,059 B2 | 9/2012 | Nardeo et al. | |
| 8,292,939 B2 | 10/2012 | Yachia et al. | |
| 8,308,789 B2 | 11/2012 | Armstrong | |
| 8,356,457 B2 | 1/2013 | Murray et al. | |
| 8,359,721 B2 | 1/2013 | Melsheimer et al. | |
| 8,382,715 B2 | 2/2013 | Nardeo et al. | |
| 8,444,686 B2 | 5/2013 | Holman et al. | |
| 8,641,752 B1 | 2/2014 | Holm et al. | |
| 8,657,789 B2 | 2/2014 | Guo et al. | |
| 8,657,866 B2 | 2/2014 | Melsheimer et al. | |
| 8,827,958 B2 | 9/2014 | Bierman et al. | |
| 8,845,712 B2 | 9/2014 | Irwin et al. | |
| 8,852,257 B2 | 10/2014 | Liu et al. | |
| 8,858,614 B2 | 10/2014 | Headley, Jr. et al. | |
| 8,889,211 B2 | 11/2014 | Owens et al. | |
| 8,919,553 B2 | 12/2014 | Murray et al. | |
| 8,932,262 B2 | 1/2015 | Osffeld et al. | |
| 9,011,512 B2 | 4/2015 | Drasler | |
| 9,061,126 B2 | 6/2015 | Fischell et al. | |

(56) References Cited

U.S. PATENT DOCUMENTS

| | | | |
|---|---|---|---|
| 9,078,781 B2 | 7/2015 | Ryan et al. | |
| 9,119,740 B2 | 9/2015 | Cannon et al. | |
| 9,168,164 B2 | 10/2015 | Dorn et al. | |
| 9,192,499 B2 | 11/2015 | Gibbons, Jr. | |
| 9,211,206 B2 | 12/2015 | Pryor | |
| 9,216,101 B2 | 12/2015 | State | |
| 2005/0245900 A1* | 11/2005 | Ash | A61M 25/0017 604/537 |
| 2005/0267562 A1 | 12/2005 | Jones et al. | |
| 2006/0020327 A1* | 1/2006 | Lashinski | A61F 2/2436 623/1.25 |
| 2006/0041277 A1* | 2/2006 | Deem | A61N 1/0551 607/3 |
| 2006/0052749 A1* | 3/2006 | Moyer | A61B 17/3421 604/160 |
| 2006/0052750 A1* | 3/2006 | Lenker | A61B 17/3439 604/164.01 |
| 2007/0016280 A1* | 1/2007 | Yacoby | A61F 2/88 623/1.11 |
| 2007/0066862 A1 | 3/2007 | Vaska | |
| 2007/0225659 A1 | 9/2007 | Melsheimer | |
| 2008/0146999 A1* | 6/2008 | Tanaka | A61M 25/10 604/96.01 |
| 2008/0208128 A1* | 8/2008 | Guo | A61M 25/0668 604/164.05 |
| 2009/0018633 A1 | 1/2009 | Lindquist et al. | |
| 2009/0018635 A1 | 1/2009 | Holman et al. | |
| 2009/0018640 A1 | 1/2009 | State | |
| 2009/0227948 A1* | 9/2009 | Chen | A61L 29/085 604/103.02 |
| 2009/0234290 A1* | 9/2009 | Fisher | A61M 25/0668 604/164.05 |
| 2010/0069839 A1 | 3/2010 | Holman et al. | |
| 2010/0069852 A1* | 3/2010 | Kelley | A61F 2/2436 604/264 |
| 2010/0100170 A1* | 4/2010 | Tan | A61F 2/94 623/1.18 |
| 2010/0249907 A1* | 9/2010 | Dorn | A61F 2/95 623/1.23 |
| 2010/0266656 A1 | 10/2010 | Johnson | |
| 2010/0298839 A1* | 11/2010 | Castro | A61B 17/3421 606/114 |
| 2010/0312261 A1 | 12/2010 | Suzuki et al. | |
| 2010/0331780 A1* | 12/2010 | Bellisario | A61B 17/3415 604/164.05 |
| 2011/0184509 A1 | 7/2011 | Von Oepen et al. | |
| 2011/0184510 A1* | 7/2011 | Maisano | A61B 17/0401 623/1.24 |
| 2011/0208284 A1 | 8/2011 | Hofmann et al. | |
| 2011/0208292 A1 | 8/2011 | Von Oepen et al. | |
| 2011/0224680 A1* | 9/2011 | Barker | A61B 17/3468 606/129 |
| 2011/0264128 A1* | 10/2011 | Mauch | A61B 17/32072 606/170 |
| 2011/0268781 A1* | 11/2011 | Cleek | A61L 29/085 424/422 |
| 2011/0301565 A1* | 12/2011 | Weber | A61M 25/10 604/500 |
| 2012/0041537 A1 | 2/2012 | Parker et al. | |
| 2012/0083740 A1* | 4/2012 | Chebator | A61M 25/0668 604/164.03 |
| 2012/0109281 A1 | 5/2012 | Papp | |
| 2012/0143138 A1* | 6/2012 | King | A61M 25/0668 604/167.03 |
| 2012/0143303 A1* | 6/2012 | Dorn | A61F 2/966 623/1.12 |
| 2012/0221089 A1* | 8/2012 | Drasler | A61F 2/962 623/1.11 |
| 2012/0277843 A1* | 11/2012 | Weber | A61F 2/958 623/1.11 |
| 2012/0296313 A1* | 11/2012 | Andreacchi | A61M 25/0668 604/509 |
| 2012/0302955 A1* | 11/2012 | Liu | A61F 2/0095 604/103.05 |
| 2012/0324696 A1* | 12/2012 | Liu | A61F 2/958 29/428 |
| 2013/0018309 A1* | 1/2013 | Ewing | A61M 25/001 604/103.05 |
| 2013/0030519 A1* | 1/2013 | Tran | A61F 2/2433 623/2.11 |
| 2013/0090624 A1* | 4/2013 | Munsinger | A61F 2/958 604/500 |
| 2013/0226276 A1* | 8/2013 | Newell | A61F 2/82 623/1.11 |
| 2013/0226279 A1 | 8/2013 | Slattery et al. | |
| 2013/0253466 A1* | 9/2013 | Campbell | A61M 25/10 604/500 |
| 2013/0274720 A1* | 10/2013 | Brannon | A61B 17/32053 606/1 |
| 2013/0296877 A1 | 11/2013 | Irwin et al. | |
| 2014/0052104 A1 | 2/2014 | Osada et al. | |
| 2014/0066904 A1 | 3/2014 | Young | |
| 2014/0120287 A1 | 5/2014 | Jacoby et al. | |
| 2014/0142681 A1 | 5/2014 | Norris | |
| 2014/0157567 A1* | 6/2014 | Wang | A61F 2/0095 29/428 |
| 2014/0157573 A1 | 6/2014 | Guo et al. | |
| 2014/0277359 A1 | 9/2014 | Slazas et al. | |
| 2014/0277362 A1 | 9/2014 | Roeder | |
| 2014/0324149 A1 | 10/2014 | Slattery et al. | |
| 2014/0336581 A1 | 11/2014 | Collin | |
| 2014/0379064 A1 | 12/2014 | Pacetti et al. | |
| 2015/0025564 A1* | 1/2015 | Tsutsui | A61M 25/1002 606/194 |
| 2015/0119922 A1 | 4/2015 | Kamel et al. | |
| 2015/0126930 A1 | 5/2015 | Bierman et al. | |
| 2015/0151087 A1 | 6/2015 | Suzuki et al. | |
| 2015/0246210 A1 | 9/2015 | Yacoby et al. | |
| 2015/0257910 A1 | 9/2015 | Duong et al. | |
| 2015/0306361 A1 | 10/2015 | Feig et al. | |
| 2016/0008583 A1 | 1/2016 | Guo et al. | |
| 2016/0022456 A1 | 1/2016 | Butler et al. | |
| 2016/0038321 A1 | 2/2016 | Shumer et al. | |
| 2016/0038713 A1* | 2/2016 | Kearns | A61M 25/002 206/210 |
| 2016/0058983 A1* | 3/2016 | Poker | A61M 25/10 604/509 |
| 2016/0158513 A1* | 6/2016 | Ryu | A61M 37/0015 604/103.02 |
| 2017/0312110 A1 | 11/2017 | Pacetti et al. | |

FOREIGN PATENT DOCUMENTS

| | | |
|---|---|---|
| JP | 2012-183401 A | 9/2012 |
| JP | 3182410 U | 3/2013 |
| WO | 1995030449 A1 | 11/1995 |
| WO | 9806452 A1 | 2/1998 |
| WO | 2006053308 A2 | 5/2006 |
| WO | 2010120425 A2 | 10/2010 |
| WO | 2011075727 A1 | 6/2011 |
| WO | 2013064215 A1 | 5/2013 |
| WO | 2014072212 A2 | 5/2014 |
| WO | 2015011712 A1 | 1/2015 |

OTHER PUBLICATIONS

Definition of Tab (Oxford Dictionary on Oct. 18, 2018).*
JP 2016-512088 filed May 2, 2014 Office Action dated Feb. 13, 2018.
NZ 714341 filed Nov. 19, 2015 Examination Report dated Feb. 5, 2018.
PCT/US2014/036693 filed May 2, 2014 International Preliminary Report and Written Opinion dated Nov. 3, 2015.
AU 2014262160 filed Nov. 19, 2015 Office Action dated Jul. 17, 2018.
JP 2016-512088 filed May 2, 2014 Office Action dated Jun. 14, 2018.

(56) References Cited

OTHER PUBLICATIONS

NZ 714341 filed Nov. 19, 2015 Examination Report dated Jul. 24, 2018.

* cited by examiner

PEELABLE PROTECTIVE SHEATH

PRIORITY

This application is a U.S. national stage application of International Application No. PCT/US14/36693, filed May 2, 2014, which claims the benefit of priority to U.S. Provisional Application No. 61/819,433, filed May 3, 2013, each of which is incorporated by reference in its entirety into this application.

BACKGROUND

Angioplasty is a procedure used for the treatment of blockages or stenosis in blood vessels, e.g., arteries. Blockages may occur from cholesterol build up on blood vessel walls or due to formation of thrombus. In angioplasty procedures, a dilatation balloon catheter is generally used in an effort to dilate the blood vessel and open up the blockage area. A balloon catheter may be inserted into a blood vessel of a patient using an introducer. The balloon catheter may be inserted through the introducer and advanced through a blood vessel until the distal end of the balloon catheter is at a desired location in the vasculature, e.g., at the site of a blockage or stenosis. A guide wire may be introduced and used to guide the balloon catheter to the desired location. The balloon catheter is advanced over the guide wire until the balloon is properly positioned. Once properly positioned in a blockage or stenosis area, an expandable balloon at the distal end of the balloon catheter may be inflated, e.g., by passing a fluid through an inflation lumen into the balloon. Relatively high pressures may be used to radially expand the balloon and dilate the lumen of the blood vessel and compress the plaque of the blockage or stenosis.

To perform angioplasty procedures, it is desirable for the balloon catheter to have a narrow profile, or relatively small deflated cross-sectional diameter so it is easier to advance the balloon catheter into a stenosis or blockage area. The balloon of the angioplasty catheter is often formed from a very thin polymeric material to provide for a narrower profile. Further, the balloon can be wrapped or folded about the shaft of the catheter into a tightly folded, deflated configuration, which helps to minimize the profile. While balloons are generally capable of developing high pressures under inflation, the balloons are delicate and can be damaged such that the balloon may fail during inflation. For example, the material of the balloons may be susceptible to scratches or other damage, e.g., during shipping and/or handling, which can result in premature balloon failure. Accordingly, it is desirable to protect the balloon from damage until it is used. A protective sheath/sleeve may be applied over the balloon to provide this protection. The protective sheath also helps to maintain the balloon in its tightly folded, low profile configuration during shipping, handling, and storage. Similar background information and more details may be found in U.S. Pat. Nos. 5,893,868 and 6,110,146, each of which is incorporated by reference in its entirety into this application.

It may be desirable to coat balloons for use in angioplasty for various purposes. For example, it may be desirable to coat balloons with bioactive agents or drugs. For example, anti-restenosis, anti-coagulant, and/or anti-thrombogenic drugs coated on an angioplasty balloon may help prevent restenosis. These coatings must also be protected (e.g., by a protective sheath). However, some coatings, e.g., drug-coatings, may be slightly adhesive or sticky causing difficulties in removal of a protective sheath from the balloon at the time of use. Protective sheaths and methods that make removal easier are desirable. Further, it is advantageous to protect the bioactive coating so its benefits may be fully realized at the treatment location, e.g., at the location of the blockage or stenosis. However, the bioactive coating may be scraped off or diminished as the balloon is inserted through an introducer, especially if the balloon must be inserted through another device, such as hemostatic valve, e.g., a hemostatic valve in the introducer. For example, the device or hemostatic valve may have edges and a concentration of force may build up at the edges as the balloon is inserted through the device or hemostatic valve, which may cause the bioactive coating to scrape off. Also, the coating can be more easily displaced, if exposed to liquid prior to insertion.

Protective sheaths, systems, assemblies, devices, methods, etc. that address these and other issues are disclosed herein.

SUMMARY

Embodiments of, and enhancements for, protective sheaths, systems, assemblies, devices, methods, etc. for protecting medical devices, including catheters and balloon catheters, are described herein.

In one embodiment, a protective sheath for protecting a balloon of a balloon catheter includes a tubular body portion comprising polymer molecules, e.g., ePTFE molecules, aligned parallel to a central longitudinal axis of the tubular body portion. The tubular body portion includes an inner lumen with an inner diameter fitted to or only slightly larger than the outer diameter of the balloon in a deflated, folded configuration. The tubular body portion is configured to hold the balloon in the deflated, folded configuration without compressing the balloon. The protective sheath also includes a first tab extending axially from the tubular body portion. The first tab may include a first textured surface on one or more sides of the tab. For example, the first tab may include a textured surface on a first side facing away from the central longitudinal axis and a second textured surface on a second side facing toward the central longitudinal axis. The protective sheath may also include a second tab that extends axially from the tubular body portion, the second tab including a first textured surface on a first side of the first tab facing away from the first tab and/or the central longitudinal axis and a second textured surface on a second side of the first tab facing toward the first tab and/or the central longitudinal axis. The first tab may include a nub on an end thereof to further enhance grippability; the nub may protrude from the first tab. The tubular body portion may or may not include a slit, scoring, or perforations running along its length, i.e., either partially or fully along the length.

In one embodiment, the tubular body portion of the protective sheath is configured to compress a first outer diameter of a balloon of a balloon catheter in a folded configuration to a second outer diameter narrower than the first outer diameter in a compressed configuration of the balloon.

In one embodiment, a system for use in angioplasty procedures includes a balloon catheter including a balloon having an outer surface coated with a bioactive agent, the balloon having a folded configuration; and a peelable protective sheath disposed over the balloon. The peelable protective sheath includes a tubular body portion including an inner lumen with an inner diameter fitted to or only slightly larger than an outer diameter of the balloon in the folded configuration, the tubular body portion configured to fit over the balloon and hold the balloon in the folded configuration without compressing the balloon, and a first tab extending axially from the tubular body portion. The first tab may include a first textured surface on one or more sides. For example, the first tab may include a textured surface on a first side of the first tab facing away from a central longitudinal axis of the tubular body portion and a second textured surface on a second side of the first tab facing toward the central longitudinal axis. A second tab may also extend axially from the tubular body portion. The second tab may include a textured surface on one or more sides. For example, the second tab may include a first textured surface on a first side of the second tab facing away from the first tab and/or the central longitudinal axis and a second textured surface on a second side of the second tab facing toward the first tab and/or the central longitudinal axis. The first tab and/or the second tab may include a nub on an end thereof to further enhance grippability; the nub may protrude from the tab(s).

In one embodiment, a method of introducing a drug-coated balloon catheter into a blood vessel includes first providing a balloon catheter assembly, wherein the balloon catheter assembly includes a balloon catheter including a balloon disposed on a distal portion of the balloon catheter, the balloon having a folded configuration and a peelable protective sheath disposed over the balloon and holding the balloon in the folded configuration without compressing the balloon. The method includes inserting the distal portion of the balloon catheter assembly through a hemostatic valve and into an introducer, such that at least a portion of the balloon and at least a portion of the peelable protective sheath are disposed within the introducer, and then peeling the peelable protective sheath to remove it from the balloon catheter. The peelable protective sheath may include a first tab and a second tab extending axially from a main body portion of the peelable protective sheath, and inserting a balloon catheter assembly leaves the first tab and the second tab outside of the hemostatic valve and the introducer. The first tab and the second tab may include textured surfaces facing away from each other and textured surfaces facing toward each other. The main body portion may include a flared region. The tabs and/or the flared region may be configured to resist entering or be unable to enter the introducer and/or the hemostatic valve to prevent the entire peelable protective sheath from entering the introducer, the hemostatic valve, and/or the blood vessel. Also, peeling the peelable protective sheath to remove it from the balloon catheter may include peeling a proximal portion of the peelable protective sheath while a distal portion of the peelable protective sheath remains within the introducer, and then sliding the distal portion proximally out of the introducer before peeling the distal portion, while leaving the at least a portion of the balloon within the introducer.

Peeling the peelable protective sheath to remove it from the balloon catheter may include grasping the first tab and a shaft of the balloon catheter with one hand, grasping the second tab with a second hand, pulling the second tab away from the first tab to peel the peelable protective sheath. Also, a distal end of the peelable protective sheath may include a tapered portion that is tapered from a larger outer diameter to a smaller outer diameter, and wherein inserting the distal portion of the balloon catheter assembly through a hemostatic valve includes directing the tapered portion through the hemostatic valve.

In one embodiment, a method of introducing a drug-coated balloon catheter into a blood vessel, includes: (1) providing a balloon catheter assembly, including a balloon catheter with a balloon disposed on a distal portion of the balloon catheter, the balloon having a folded configuration, and a peelable protective sheath disposed over the balloon and holding the balloon in the folded configuration without compressing the balloon; (2) peeling a distal portion of the peelable protective sheath away from the balloon catheter to expose an exposed distal portion of the balloon catheter; (3) inserting the exposed distal portion of the balloon catheter through a hemostatic valve and into an introducer; (4) peeling an additional portion of the peelable protective sheath away from the balloon catheter to expose an exposed additional portion of the balloon catheter; (5) inserting the exposed additional portion of the balloon catheter through the hemostatic valve and into the introducer; (6) repeating steps (4)-(5) until the balloon has entirely passed through the hemostatic valve; and (7) peeling and removing any remaining portion of the peelable protective sheath from the balloon catheter.

In one embodiment, a method of manufacturing a peelable protective sheath, includes extruding a tubular body comprising a polymeric material, cutting one end of the tubular body along a diameter line in a direction along a limited length of the tubular body to form two semi-circular body portions of equal size that extend axially from an uncut tubular main body portion, and flattening and imparting textured surfaces to a portion of the semi-circular body portions to form two tabs with textured surfaces.

BRIEF DESCRIPTION OF THE DRAWINGS

The disclosed devices, systems and methods can be better understood with reference to the following drawings. The components in the drawings are not necessarily to scale.

Figure 1:
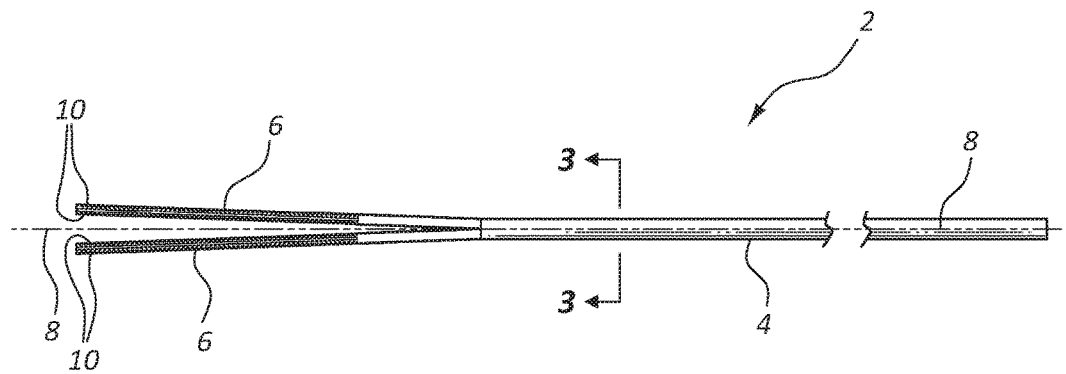
FIG. 1 shows a side view of an exemplary peelable protective sheath.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The following description and accompanying figures, which describe and show certain embodiments, are made to demonstrate, in a non-limiting manner, several possible configurations of peelable protective sheaths, catheter assemblies and systems, and various methods of using them according to various aspects and features of the present disclosure.

Various systems, assemblies, devices, and methods are described herein, including balloon catheter systems, assemblies, and devices for use in angioplasty procedures. While specific embodiments are discussed below by way of example, the embodiments and examples described are not intended to be limiting. Accordingly, the disclosure is not limited to balloon catheter assemblies, protective sheaths for protecting balloons of balloon catheters, or angioplasty devices or systems/assemblies in general. Rather, the inventive principles associated with the embodiments described herein, including with respect to the balloon catheter systems/assemblies, peelable protective sheaths, methods, etc. described herein, may be applied to other types of protective sheaths/sleeves, other medical devices, other assemblies and systems, other methods, etc.

Figure 2:
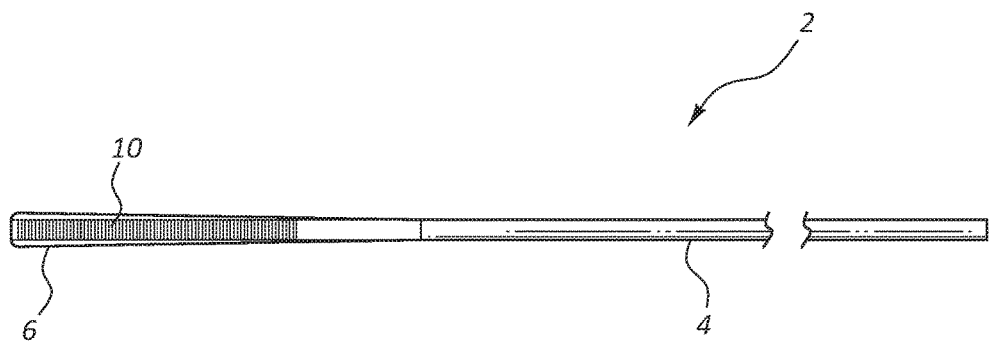
FIG. 2 shows a top view of the exemplary peelable protective sheath of FIG. 1.
Figures 3A, 3B:
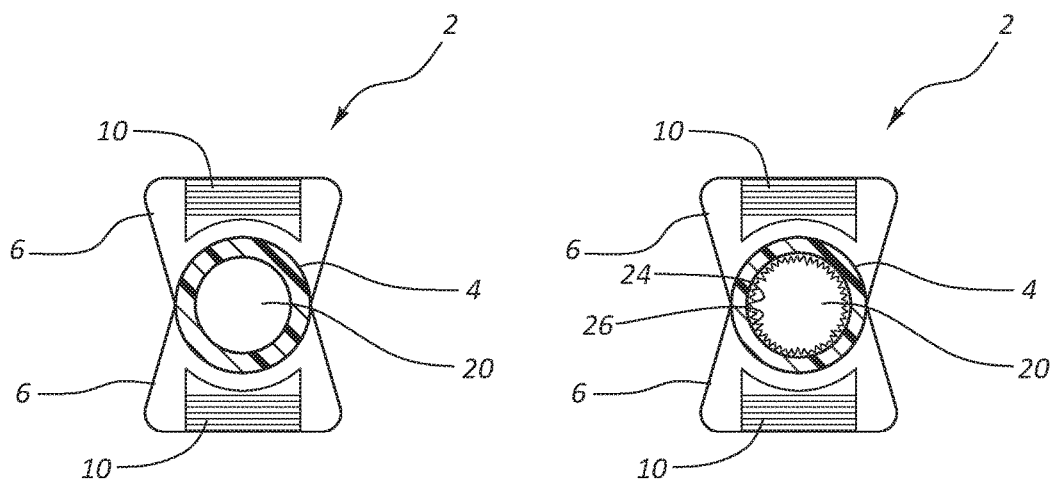
FIGS. 3A and 3B show views of the exemplary peelable protective sheath of FIG. 1 as if cut along the line at 3-3 in FIG. 1 and viewed looking down the central longitudinal axis in the direction indicated by the arrows at 3-3.

In one embodiment, a system/assembly for use in angioplasty procedures may include a peelable protective sheath and a balloon catheter including a balloon. The balloon and/or shaft of the balloon catheter may have an outer surface coating, e.g., a lubricious coating, hydrophobic coating, hydrophilic coating, polymer coating, surfactant coating, radiopaque coating, echogenic coating, fluoroscopic coating, iopromide coating, etc. Optionally, the coating may include a bioactive agent/drug. Some bioactive agents/drugs that may be coated on the balloon catheter include, without limit, anti-thrombogenic drugs, anti-restenosis drugs, anti-coagulant drugs, anti-inflammatory drugs, Paclitaxel, Everolimus, Zotarolimus, Sirolimus, Dextran, Rapamycin, Prostacyclin, tacrolimus, batimastat, halofuginone, interferon, dexamethasone, cyclosporine, Heparin, similar drugs, etc. The balloon may have an expanded configuration and a deflated, folded configuration (the balloon may be arranged in a low profile configuration by different means, e.g., by wrapping, folding or otherwise arranging the balloon, but low profile arrangements are generally referred to herein, in a non-limiting way, as a "folded configuration" or a "deflated, folded configuration") . The deflated, folded configuration having a diameter smaller than the diameter of the expanded configuration. The balloon may transition from the deflated, folded configuration to the expanded configuration when a fluid (e.g., water, saline solution, air, etc.) is passed through an inflation lumen into the balloon. Optionally, the balloon catheter may have collapsed stent disposed over the balloon; the stent may be expanded and delivered by expansion of the balloon. A peelable protective sheath, e.g., peelable protective sheath 2 (as shown in FIGS. 1-3), may be applied over the top of the distal portion of the balloon catheter and the balloon in its deflated, folded configuration. If a stent is disposed over the balloon, then the protective sheath may be applied over the top of the stent as well. When disposed over the folded balloon, the peelable protective sheath 2 helps to hold the balloon in the folded configuration and maintains a narrow profile of the assembly and/or system. If a stent is used, then the peelable protection sheath can also help hold the stent in the collapsed or narrower configuration and protect the stent and any coating thereon.

FIGS. 1 and 2 illustrate a side view and a top view, respectively, of an exemplary peelable protective sheath 2. The terms: protective sheath, protective sleeve, protection sheath, protection sleeve, balloon protector, and the like are used synonymously herein. Peelable protective sheath 2 may be used for protecting the balloon of a balloon catheter, e.g., an angioplasty balloon dilatation catheter. Also, peelable protective sheath 2 may be used to protect a coating on a balloon catheter, e.g., a bioactive/drug coating on a balloon of a balloon catheter, as discussed above. However, the inventive principles associated with peelable protective sheath 2 may be applied to other types of protective sheaths/sleeves, other medical devices, other catheter assemblies and systems, etc.

As shown in FIGS. 1-3, peelable protective sheath 2 may include a tubular main body portion 4 and tabs 6 extending axially therefrom. As can be seen in FIG. 3, tubular body portion 4 is tubular in shape and includes an inner lumen 20. FIG. 3 shows a view of peelable protective sheath 2 as if cut along the line at 3-3 in FIG. 1 and viewed looking down the central longitudinal axis 8 toward tabs 6, i.e., in the direction indicated by the arrows at 3-3. As can be seen in FIG. 3, the tubular main body portion 4, shown in cross section at the center of FIG. 3, is tubular in shape. Peelable protective sheath 2 may be open at its distal end such that a guide wire may be fed into a catheter the protective sheath is disposed over; the end user, e.g., a clinician or doctor, may hold onto the peelable protective sheath when loading the guide wire so as not to touch the catheter or a bioactive coating on the catheter. In one embodiment, tubular main body portion 4 has a constant outer diameter, constant inner diameter, and/or constant wall thickness within manufacturing tolerances along its entire length from its distal end to its proximal end.

Optionally, tubular main body portion 4 may include a flared region or more than one flared region with a larger outer diameter and/or inner diameter. The flared region may occur at the proximal end of the tubular main body portion 4, at the distal end of the tubular main body portion 4, or both. The flare or flared region may assist with application to the device by providing a funneling effect as the peelable protective sheath is applied to or loaded on the balloon. Additionally, by having a flared region at one or both of the ends of the tubular main body portion 4, the profile of the central region of the peelable tubular main body portion 4 may be reduced without hindering easy application of the peelable protective sheath. Similarly, if the flared region is only at the proximal end of the tubular main body portion, then the distal end of the main body portion may have a narrower profile, which makes it easier to use when inserting the distal end into an introducer and/or hemostatic valve as discussed below. Also, portions or folds of the folded balloon may sometimes extend radially outward and cause the peelable protective sheath to begin peeling prematurely as the peelable protective sheath is loaded onto the balloon. A flared region may help to hold in and guide the flaps of the balloon and thereby prevent premature propagation of peeling. Similarly, if the balloon expands over time, it may be harder to apply the protective sheath and may cause premature splitting, but a flared region may help alleviate this problem. Further, the flared region may be used to force the balloon into a tighter or narrower folded configuration as it funnels the balloon to the narrower profile region of the protective sheath.

A flared region may be added to the tubular body using a bump extrusion procedure as the tubular body is extruded. Alternatively, an end of the tubular body may be heated to make it more malleable, and a device (e.g., a conical shaped pin or needle) may then be used to create the flared region in the heated tubing. Tubular main body portion 4 may have a non-flared region(s) with a constant outer diameter, constant inner diameter, and/or constant wall thickness within manufacturing tolerances along its length between any flared region(s), tapered region(s), and/or its distal and proximal ends. In one embodiment, the flared region may have an inner diameter that is 1.2 to 2 times larger than the inner diameter of a non-flared region.

In one embodiment, the inner diameter of inner lumen 20 of the protective sheath is configured to be only slightly larger (e.g., about 0.03 inches or less), at least in the region of tubular main body portion 4 that covers the balloon of the balloon catheter, than the outer diameter of the balloon of a balloon catheter when the balloon is in a deflated, folded configuration. In one embodiment, the inner diameter of inner lumen 20 in the region covering the balloon is between about 0.005 inches to about 0.010 inches larger than the outer diameter of the balloon in its initial folded configuration, i.e., shortly after folding. By having the inner diameter of the inner lumen 20 be only slightly larger than the balloon in an initial deflated, folded configuration, the tubular body portion may be configured to hold the balloon in a deflated, folded configuration without compressing the balloon, i.e., without compressing/forcing the balloon to an outer diameter smaller than the deflated, folded configuration or smaller than the initial folded configuration shortly after folding. It is noted that the outer diameter of the folded balloon may expand or increase somewhat over time and/or during subsequent processing, so the peelable protective sheath should generally be applied to the balloon shortly after initial folding. Then, even if the outer diameter of the balloon tends to expand or increase over time, the peelable protective sheath can hold the folded balloon to a narrower profile. If a stent is used over the balloon and the protective sheath is placed over the balloon and stent, then the protective sheath may have an inner diameter that is about 0.05 inches or less larger than the outer diameter of the combined stent and balloon.

Optionally, the peelable protective sheath 2 may be fitted to match the size of the balloon in the folded configuration (e.g., in the initial folded configuration) or the size of a combined balloon and stent. In one embodiment, the inner diameter of the protective sheath is fitted to or close in size to the profile of the balloon in its initial folded configuration (i.e., right after folding). If a stent is used over the balloon and the protective sheath is placed over the balloon and stent, then the protective sheath may have an inner diameter that is fitted to the outer diameter of the balloon and stent combination or assembly. This fitting and matching of sizes helps to beneficially maintain a lower profile.

Alternatively, the peelable protective sheath 2 may be designed to compress/force the balloon to a smaller outer diameter (e.g., to a diameter smaller than the initial folded configuration), which may beneficially improve (i.e., narrow) the profile of the balloon catheter and protective sheath assembly. However, damage can occur to the balloon if it is subject to compressive forces. Also, various methods used to initiate compression of the protective sheath around the balloon can also cause damage to the balloon or the bioactive coating on the balloon, e.g., if heat is applied to initiate compression, the heat may weaken the balloon or adversely affect the coating or bioactive agents in the coating. Also, if the sheath compresses the folded balloon to hold a tighter profile, the balloon may exert outward force on the sheath as it tends to expand over time that may cause premature peeling.

In view of the above, it is sometimes desirable to manufacture the inner diameter of the inner lumen 20 to be slightly larger than the outer diameter of the balloon in the deflated, folded configuration (as discussed above) to avoid compressing the balloon and avoid methods of initiating compression, while maintaining an overall profile of the assembly that is nonetheless relatively narrow. Further, having a peelable protective sheath that does not compress the balloon also eliminates a manufacturing step (i.e., initiating compression) and can make it easier to remove the peelable protective sheath. Additionally, having an inner diameter slightly larger than the outer diameter of the balloon in the folded configuration makes it easier to apply the peelable protective sheath to the balloon catheter (or combined balloon and stent). Further, if coated, the coated portion of the balloon and/or stent may be sticky, slightly adhesive, and/or otherwise resistant to application of the protective sheath, and a somewhat larger inner diameter makes application over the coating easier. Smaller diameter balloons generally require less over-sizing of the inner diameter of the protective sheath than larger diameter balloons.

Optionally, an inner surface of the inner lumen may be roughened such that the inner surface of the inner lumen has a reduced surface area in contact with the balloon and/or catheter, which can help make application and removal of the peelable protective sheath 2 to the balloon and/or catheter easier. For example, the inner surface may include a roughness characterized by a series of essentially peaks and valleys, wherein the valleys are configured such that they do not directly contact the balloon while peaks adjacent to the valleys are configured such that they do directly contact the balloon. The roughened surface and/or the peaks and valleys may have an ordered pattern (e.g., peaks and valleys extending along the length of the sheath parallel to the longitudinal axis of the sheath) or may be randomly arranged (e.g., a random texture similar to a gravel road). This roughness may be imparted to the inner surface during extrusion.

Optionally, tubular body portion 4 may include a tapered distal end, the tapered distal end being configured for insertion through a hemostatic valve of an introducer. The tapered distal end in one embodiment tapers from a larger outer diameter to a smaller outer diameter in a proximal to distal direction. The smaller diameter would facilitate easier insertion of the distal end of the protective sheath 2 into the introducer and/or hemostatic valve.

Tubular body portion 4 may be constructed of a polymeric material. The polymeric material may be expanded polytetrafluoroethylene (ePTFE), high-density polyethylene (HDPE), Pebax (e.g., Pebax 7233), Nylon (e.g., Nylon 12), polyethylene terephthalate (PET), polytetrafluoroethylene (PTFE), or a combination of two or more of these materials. The polymeric material can be extruded to form the tubular body portion 4 and/or tabs 6. The polymer molecules in the tubular body portion 4 may be aligned/oriented parallel to a central longitudinal axis 8 of the tubular body portion 4. This alignment/orientation may be done during extrusion, via stretching during extrusion or after extrusion, using E-Beam sterilization procedures, and/or cold drawing the polymeric material. By orienting or aligning the polymer molecules parallel to central longitudinal axis 8, the tubular body portion 4 will tend to peel in roughly a straight line along the length of the tubular body parallel to the central longitudinal axis 8. Orienting/aligning the polymer molecules in this way is beneficial at least because it eliminates the need for a slit or weakened area/line along the side(s) of the tubular body portion 4 to obtain a good peel along the length of the tubular body portion 4. Optionally, a lubricious coating may be applied to an outer surface of the peelable protective sheath 2, e.g., the entire outer surface of the tubular body portion 4, which may ease insertion of the peelable protective sheath 2 into an introducer and/or hemostatic valve.

While a slit or otherwise weakened area is not necessary if the polymer molecules are properly aligned/oriented, the tubular body portion may optionally include a slit, scoring, perforations, wires, or wire-like features that extend the full length of the tubular body portion 4 from end to end. Also, the tubular body portion may optionally include a slit, scoring, perforations, wires, or wire-like features that extend or run partially along the length of the tubular body portion, e.g., the slit, scoring, perforations, wires, or wire-like features beginning at a first end of the tubular body portion proximate the tabs 6 and terminating before reaching a second end of the tubular body portion.

Figure 8:
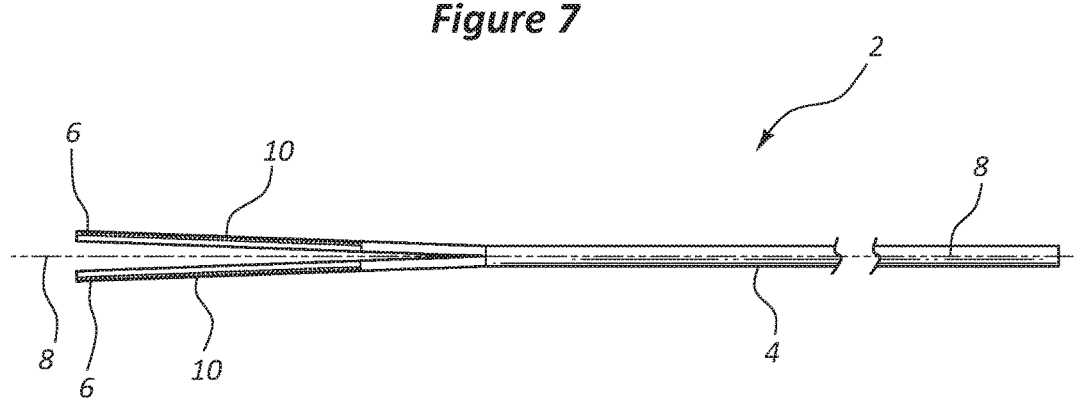
FIG. 8 shows a side view of another exemplary peelable protective sheath that has textured surfaces on only one side of each tab.
Figure 9:
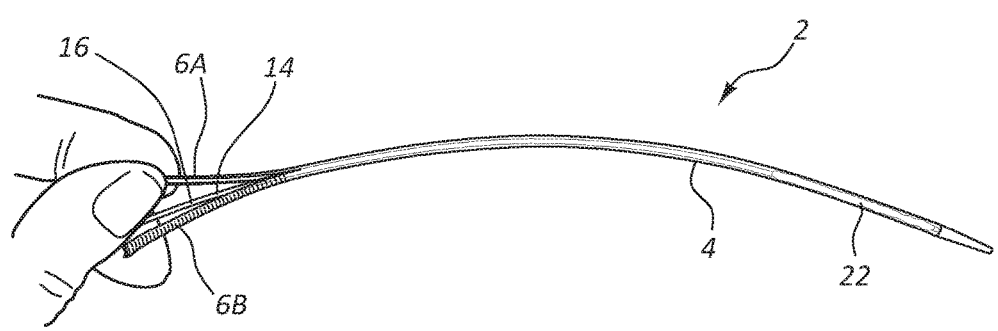
FIG. 9 shows a side view of another exemplary peelable protective sheath including a tubular body portion with a tapered distal end.
Figure 10:
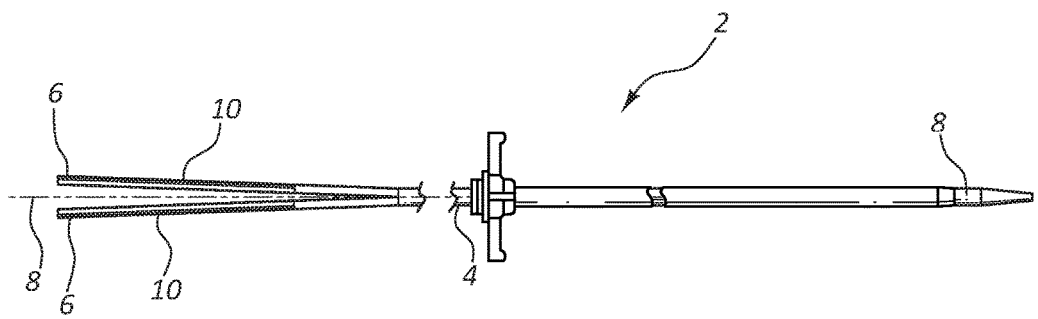
FIG. 10 shows an exemplary peelable protective sheath including an introducer having a hemostatic valve.
Figure 11:
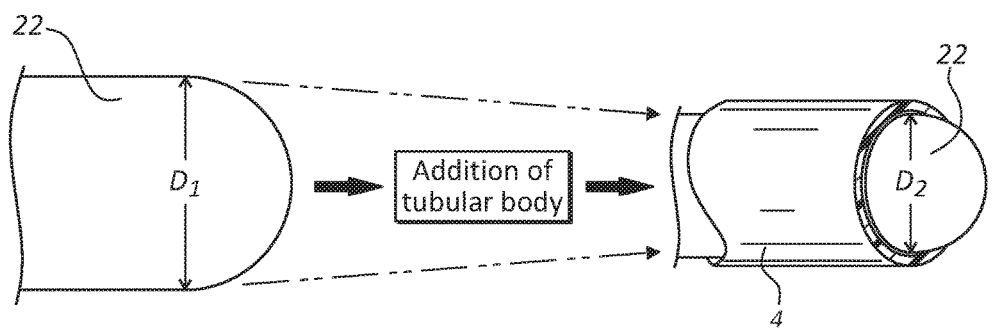
FIG. 11 illustrates that a tubular body portion of an exemplary peelable protective sheath compresses a balloon from a first outer diameter to a narrower second outer diameter.
Figure 12:
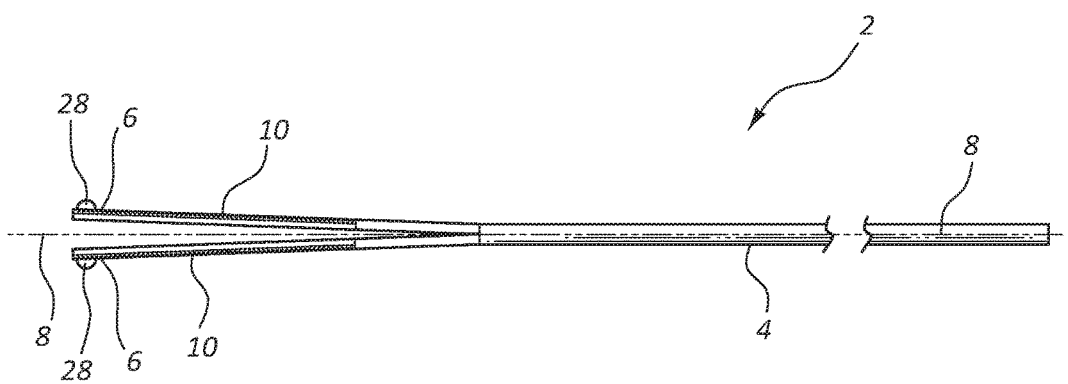
FIG. 12 shows a side view of another exemplary peelable protective sheath that includes a nub on an end of each tab.

A single tab or multiple tabs 6 may extend from either the proximal end or the distal end of the tubular main body portion 4 to aid in gripping and peeling the peelable protective sheath 2. Alternatively, no tabs may be used and another means of gripping the peelable protective sheath and/or propagating the peeling of the peelable protective sheath may be used. In FIG. 1, two tabs 6 are depicted as extending axially (or generally in a direction roughly parallel to the central longitudinal axis 8) from the tubular main body portion 4. The tabs 6 may include a textured surface 10 on one side (e.g., as shown in FIG. 8) or on both sides (e.g., as shown in FIG. 1) of each tab. For example, as shown in FIG. 1, each tab may include a first textured surface on a first side facing away from the central longitudinal axis and a second textured surface on a second side facing toward the central longitudinal axis. The tab may include a first textured surface on a first side facing away from the central longitudinal axis in a direction perpendicular to the central longitudinal axis and a second textured surface on a second side facing toward the central longitudinal axis in a direction perpendicular to the central longitudinal axis. In one embodiment, as depicted in FIG. 1, two tabs 6 may be used, each tab including a textured surface 10 on both sides of each tab, e.g., the first tab and the second tab may each include textured surfaces 10 facing away from each other and/or the central longitudinal axis 8 and textured surfaces 10 facing toward each other and/or the central longitudinal axis 8. Textured surfaces 10 aid in gripping the tabs 6, and the tabs 6 act to initiate and propagate peeling of the peelable protective sheath 2. Tabs 6 may be made from the same material or a different material from the tubular body portion 4. In one embodiment, a nub 28 as depicted in FIG. 12, or the like, may be incorporated on the ends of the tab(s) as another gripping feature. The textured surfaces and gripping feature described above can enhance grippability of the tabs when peeling the protective sheath and prevent fingers from sliding off of the tabs when pulling them.

Similarly, if a flared region, as discussed above, were used on an end of the tubular main body portion 4, the tabs 6 would extend axially from the flared region. However, it is noted that a flared region is not necessary when tabs similar to tabs 6 are used, because tabs 6 may be pulled apart somewhat to act similar to a flared region and guide the balloon, including its folds, into the tubular main body portion. One would need to be careful not to pull so hard as to cause premature propagation of peeling, but could guide the tabs 6 outwardly to create a funnel like shape to help funnel the balloon into the tubular main body portion 4. Accordingly, benefits similar to those described above with respect to adding a flared region may be provided by the tabs 6 themselves, at least in part.

Optionally, the tabs 6 may be reinforced or otherwise treated to strengthen and/or stiffen the tabs 6. For example, the tabs 6 may be manufactured from a first material and reinforced with a second material different from the first material. The second material or reinforcement material may include a wire, wire-like material, thread, layer(s) of other materials, stiffened plastic material, etc. Optionally, the tabs 6 may be reinforced by additional layers of the same material as the tabs and/or tubular body are made from, or the tabs may be manufactured/extruded to have a single wall layer that is thicker than the walls of tubular body portion 4.

One method of manufacturing peelable protective sheath 2 involves first extruding an elongated tubular body comprising a polymeric material (e.g., one of the polymeric materials discussed above), then cutting an end of the elongated tubular body a limited distance from the end along the length of the elongated tubular body in a direction toward the opposite end of the elongated tubular body. The cut may span the diameter of the tubular body (i.e., so the circular cross section of the elongated tubular body is cut into two semi-circular cross sections), and form two semi-circular body portions of roughly equal size and each the length of the limited distance of the cut along the length. The cut may be done using various tools and methods, e.g., a radio-frequency (RF) process, a laser, a scalpel, knife, or other cutting tool. Other cuts may also be used, e.g. to produce divisions for tabs of different sizes rather than divisions/body portions of roughly equal semi-circular size.

After cutting, the semi-circular body portions extend axially from the uncut tubular main body portion. At least a portion of the semi-circular body portions may then act as tabs. To make the semi-circular body portions easier to use as tabs, the entire semi-circular body portions or a more limited region/portion thereof may be flattened and have textured surfaces added thereto. Textured surfaces may be imparted to a region/portion of the semi-circular body portions or tabs to form tabs with textured surfaces on one or both sides. The textured surfaces may be imparted to the tabs using an RF process using thermal mold, and/or by pinching the tabs between a hard device with opposing textured surfaces, or other means. Alternatively, the tabs may be manufactured separately from the tubular body and subsequently attached to the tubular body through known methods and means of attachment.

In one embodiment, a system and/or assembly using a protective sheath, e.g., peelable protective sheath 2, may also include an additional outer sleeve disposed over the protective sheath and at least a portion of the balloon catheter. This additional outer sleeve may help protect the protective sheath during packaging and shipping, and may help to prevent premature peeling of the protective sheath. The additional outer sleeve may be slid off the protective sheath and balloon catheter prior to use of the catheter and protective sheath. The additional outer sleeve is particularly helpful when using a protective sheath having a scored, perforated, slitted, or similarly weakened area. The scored, perforated, slitted, or similarly weakened area may be prone to early separation or splitting over time, e.g., if the folded balloon expands somewhat over time (e.g., as discussed above) and/or if the packaging is subject to rough shipping/handling conditions. This is especially true if the sheath compresses the folded balloon to hold a tighter profile.

Having an additional or secondary outer sleeve holds the protective sheath together and strengthens it to prevent premature splitting or propagation. The secondary outer sleeve or sheath could be slid over the peelable protective sheath. Optionally, the secondary outer sleeve or sheath may be crimped on or shrink fit over the peelable protective sheath. If a secondary outer sleeve is used, it may be removed by the end user, e.g., a clinician or doctor, by sliding it proximally or distally off the peelable protective sheath, or it may be peelable similar to the peelable protective sheath.

It is noted that in embodiments that do not have a scored, perforated, slitted, or similarly weakened area along the length of the protective sheath, an additional outer sleeve may be unnecessary (though one can optionally be used). Accordingly, a tubular main body portion (e.g., tubular main body portion 4 shown in FIGS. 1-6) that does not have a scored, perforated, slitted, or similarly weakened area along its length, or at least along the region of the tubular main body portion that is disposed directly over the area of the balloon, provides at least the advantages of added strength and avoidance of premature splitting or propagation without an additional or secondary outer sleeve. Further, the profile of a peelable protective sheath without a scored, perforated, slitted, or similarly weakened area may be narrower than a protective sheath with a weakened area, because a weakened area is more likely to prematurely split if the balloon expands somewhat. Conversely, the profile of a protective sheath with a weakened area must generally have a larger profile to help prevent this premature splitting, e.g., to accommodate some expansion. Also, the additional processing step of adding a scored, perforated, slitted, or similarly weakened area to the protective sheath is eliminated in embodiments, like those shown in FIGS. 1-6, that do not have a scored, perforated, slitted, or similarly weakened area along the tubular main body portion. As discussed above, if the polymer molecules are properly aligned, splitting of the sheath propagates easily and roughly straight without a weakened area.

Optionally, multiple protective sheaths may be disposed at different locations along the length of the balloon catheter. For example, in one embodiment, the system and/or assembly includes a first peelable protective sheath and a second peelable protective sheath disposed adjacent to each other along the balloon catheter, such that a proximal end of the first peelable protective sheath abuts a distal end of the second peelable protective sheath, without any radial overlapping between the first peelable protective sheath and the second peelable protective sheath. However, in one embodiment, there is some limited radial overlap of the proximal end of the first peelable protective sheath with the distal end of the second peelable protective sheath, while the majority of the lengths of the first peelable protective sheath and the second peelable protective sheath do not radially overlap. Having two or more peelable protective sheaths disposed along the length of the balloon catheter provides the end user, e.g., a doctor or clinician, with additional flexibility in deciding how to use and remove the peelable protective sheaths when introducing the balloon catheter into a patient. In one embodiment, a distal peelable protective sheath, e.g., the first peelable protective sheath above, may optionally have tabs similar to those discussed elsewhere herein at its distal end. In one embodiment, a proximal peelable protective sheath, e.g., the second peelable protective sheath above, may optionally have tabs similar to those discussed elsewhere herein at its proximal end. Further, these multiple protective sheaths may each include other features of the other protective sheaths discussed above.

An exemplary method of introducing a drug-coated angioplasty balloon catheter into a blood vessel involves providing a balloon catheter assembly, including a balloon catheter with a balloon disposed on a distal portion of the balloon catheter, and a peelable protective sheath disposed over the balloon. The balloon may include a bioactive coating, similar to the bioactive coatings discussed above. The balloon includes an expanded configuration and a folded configuration having an outer diameter smaller than an outer diameter of the balloon in the expanded configuration. In one embodiment, the peelable protective sheath may hold the balloon in the folded configuration without compressing the balloon, e.g., without active compression of the balloon into a diameter smaller than the diameter of the folded configuration prior to applying the protective sheath around the balloon, or without extra compression beyond merely holding the balloon in profile. If the balloon tends to expand over time, the peelable protective sheath holds the profile of the assembly and prevents the balloon from over expanding. While this may impart holding forces (or forces resistant to the expansion forces of the balloon) to hold/maintain the balloon in a low profile, it does not involve actively compressing the balloon to a smaller diameter but merely inhibits expansion of the balloon to a larger diameter. In one embodiment, the peelable protective sheath may compress the balloon, e.g., actively compressing the balloon into a diameter smaller than the diameter of the initial folded configuration (i.e., the folded configuration just prior to applying the protective sheath around the balloon), or imparting extra compression beyond merely holding the balloon to prevent expansion of the balloon.

An introducer for introducing a balloon catheter into a blood vessel of a patient may also be provided. The introducer may be equipped with a hemostatic valve, e.g., to prevent back flow of blood out of the blood vessel through the introducer. In one embodiment, the hemostatic valve is disposed at a proximal end of the introducer. While the disclosure describes, by way of non-limiting example, a hemostatic valve associated with and/or connected to an introducer, other devices/attachments may be attached to an introducer and used in connection with a protective sheath in ways similar to those described herein with respect to the hemostatic valve.

The distal portion of the balloon catheter assembly may be inserted through the hemostatic valve and into the introducer, such that at least a portion of the balloon and at least a portion of the peelable protective sheath are disposed within the introducer. In one embodiment, the entire balloon and a distal portion of the peelable protective sheath covering the balloon are inserted through the hemostatic valve before beginning to peel the peelable protective sheath from the balloon catheter. In one embodiment, only a distal portion of the balloon and a distal portion of the peelable protective sheath covering the distal portion of the balloon are inserted through the hemostatic valve before beginning to peel the peelable protective sheath from the balloon catheter. A distal end of the peelable protective sheath may optionally include a tapered portion that is tapered from a larger outer diameter to a smaller outer diameter in a proximal to distal direction, and one may direct the tapered portion through the hemostatic valve. The tapered portion facilitates easier insertion of the distal portion of the assembly/system, including the balloon catheter and peelable protective sheath.

One advantage of a peelable protective sheath adapted/configured for insertion into an introducer and/or valve, and one advantage of methods involving inserting a peelable protective sheath into an introducer and/or through a valve while disposed over the balloon and/or catheter is that it protects the balloon, catheter, and/or any coating thereon from being damaged, e.g., it prevents any bioactive coating from being scrapped off, rubbed off, or otherwise diminished during insertion. For example, a hemostatic valve may include edges or constrictions around a narrow opening that tend to scrape along the balloon and/or catheter, which may cause damage to the balloon, catheter, and/or any coating thereon and may scrape or rub off portions of the coating. Indeed, there is often a concentration of force at the edges because it is a small area at the point where the balloon catheter is pushed into the introducer. However, a peelable protective sheath configured for insertion into the hemostatic valve while disposed over the balloon catheter can protect the balloon, catheter, and coating. Also, the coating can be more easily displaced or diminished, if exposed to liquid prior to insertion. Leaving the protective sheath on the balloon catheter during insertion can prevent or limit exposure to liquid, thereby further protecting the coating. Also, leaving the protective sheath on can act as a reminder to the end user that he/she should avoid wetting the coating.

While the portion of the balloon and the portion of the peelable protective sheath are disposed within the introducer, the end user may begin to peel the peelable protective sheath starting at the proximal end of the peelable protective sheath. The peeling may be done while a distal portion of the peelable protective sheath remains within the introducer. The peelable protective sheath may then be peeled to the point at which the peelable protective sheath enters the hemostatic valve, or a short distance, e.g., less than 2 inches or less than 1 inch, before it enters the hemostatic valve (i.e., proximal of the portion of the protective sheath in the hemostatic valve).

In one embodiment, the peelable protective sheath may include a tab or tabs, e.g., a first tab and a second tab, extending axially from a main body portion of the peelable protective sheath. The tab or tabs may be similar to the tabs of peelable protective sheath 2 discussed above and/or shown in FIGS. 1-3. The tab or tabs may include textured surfaces as discussed above, for example, a first tab and a second tab may each include textured surfaces facing away from each other and textured surfaces facing toward each other. When the balloon catheter assembly is inserted through the hemostatic valve, the tab or tabs are left outside of, e.g., proximal of, the hemostatic valve and the introducer. The tab or tabs may be used to initiate and propagate the peeling of the peelable protective sheath.

Figure 4:
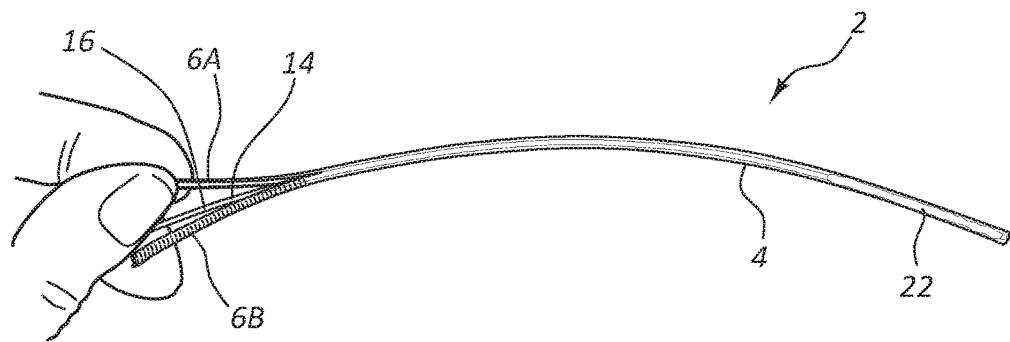
FIGS. 4-6 illustrate steps in a method of peeling a peelable protective sheath.
Figure 5:
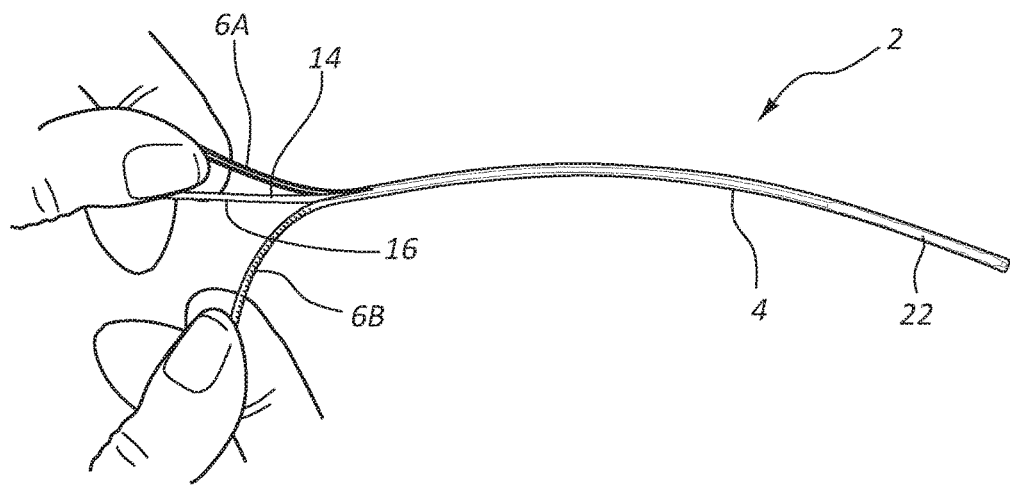
Figure 6:
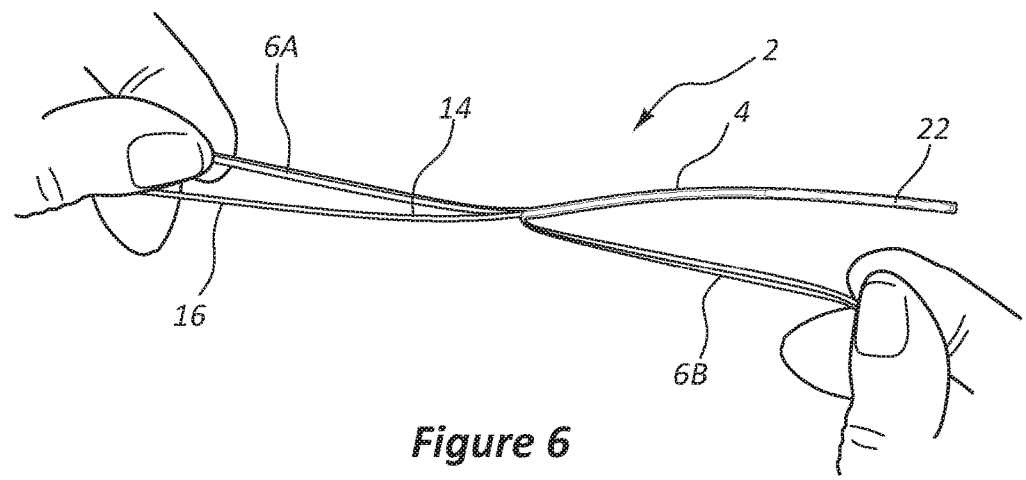
Figure 7:
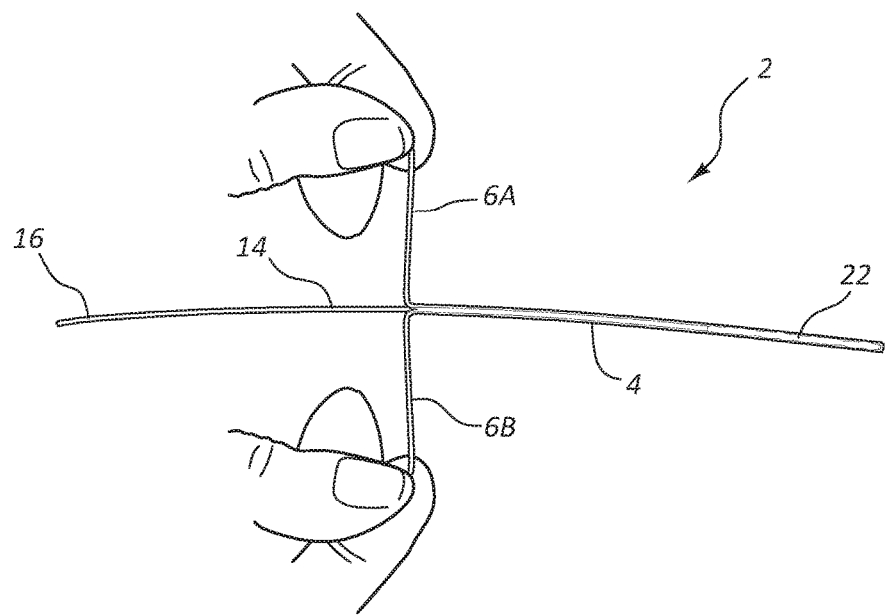
FIG. 7 illustrates peeling a peelable protective sheath wherein the person peeling the peelable protective sheath does not hold onto the balloon catheter.

FIGS. 4-6 illustrate one method of peeling a peelable protective sheath, e.g., peelable protective sheath 2. As shown in FIG. 4, one may first grasp a first tab 6A or other gripping portion of the peelable protective sheath 2 and a shaft 16 of the balloon catheter 14 with one hand. An inflatable balloon 22 is shown at the distal end of the balloon catheter 14 (while balloon 22 is shown with one possible length, the peelable protective sheaths described herein may be used with a variety of different lengths of balloons and are well suited to protecting very long balloons). As shown in FIG. 5, one may then grasp a second tab 6B or a different gripping portion of the peelable protective sheath 2 with a second hand. As depicted in FIG. 6, once the tabs 6A and 6B or gripping portion are held in opposite hands, the tabs 6A and 6B or gripping portion are pulled in different directions, e.g., the second tab 6B may be pulled away from the first tab 6A and shaft 16 to peel the peelable protective sheath. Holding the shaft 16 of the balloon catheter 14 in one hand with one of the tabs adds stability, can help reduce the risk of damaging or kinking the balloon catheter if properly handled, and can reduce the number of hands needed to safely peel the sheath. However, the peelable protective sheath may also be peeled by pulling opposite tabs or gripping portions in opposite directions without holding onto the balloon catheter in either hand, as shown in FIG. 7. If the balloon catheter is not held in either hand, it may be desirable to stabilize the balloon catheter by having a second person hold the balloon catheter, or by first loading a guidewire into the balloon catheter before peeling. Peeling the sheath when the assembly is loaded onto a guidewire may also help to stabilize the device while peeling, without needing to hold onto the shaft. Peeling can occur from two initiation points to peel the peelable protective sheath into two pieces, e.g., as discussed above using two tabs. Also, peeling can optionally occur from one initiation point, e.g., such that peeling generates a slit for the balloon to exit.

Optionally, the peelable protective sheath may be peeled from the balloon catheter using one hand. For example, if the peelable protective sheath has only one tab or one initiation point, the single tab or area of the initiation point may be pulled with one hand away from the balloon catheter and/or the remainder of the peelable protective sheath to peel the peelable protective sheath. Optionally, the shaft of the balloon catheter and/or the remainder of the peelable protective sheath may be held in one hand while another hand is used to pull and peel the peelable protective sheath from the balloon catheter. For example, the one tab or an end of the peelable protective sheath may be pulled away with one hand from the shaft of balloon catheter, which is held in another hand, to help the shaft of the balloon catheter split and exit the protective sheath. If the peelable protective sheath has two or more tabs, one may pull on only one of the tabs to peel the protective sheath with one hand.

In one embodiment, peeling is propagated linearly or longitudinally along the length of the peelable protective sheath (see e.g., FIG. 6). Indeed, orienting or aligning the polymer molecules parallel to the central longitudinal axis, as discussed above, will lead to a linear, longitudinal propagation during peeling. However, peeling could optionally be configured to propagate in other ways, e.g., in a corkscrew-like fashion. Peeling may be propagated from a distal end or a proximal end, and peeling of the protective sheath may be done incrementally or all at once.

After peeling the protective sheath a distance from the proximal end of the peelable protective sheath toward the distal end, e.g., after peeling the sheath to the point at which it enters the hemostatic valve or a short distance before this point, the peelable protective sheath may be slid proximally relative to the balloon catheter to remove a more distal portion of the protective sheath from the introducer and/or hemostatic valve. The protective sheath is slid proximally while leaving at least a portion of the balloon or the entire balloon within the introducer. Sliding the peelable protective sheath proximally to remove it from the introducer and/or hemostatic valve may be done incrementally or all at once. For example, if the peelable protective sheath is slid incrementally back or proximally, the end user may continue to peel the sheath further in between increments of sliding the peelable protective sheath proximally. Indeed, the peelable protective sheath can be slid proximally a short distance (e.g., one or two inches), then peeled to a point closer to the hemostatic valve or the distal end of the protective sheath, then slid proximally another short distance (e.g., one or two inches), then peeled again to a point closer to the hemostatic valve or the distal end of the protective sheath, and so on. These incremental steps can be repeated until the peelable protective sheath is removed from the balloon catheter. If the peelable protective sheath is slid back all at once, the entire distal portion of the protective sheath distal of the hemostatic valve, e.g., in the introducer, may be slid proximally until it exits the introducer and hemostatic valve, then the peelable protective sheath may be peeled and removed from the balloon catheter.

To slide the peelable protective sheath proximally (whether incrementally or all at once), the end user may pull proximally on the tabs and/or another portion of the peelable protective sheath that is proximal the hemostatic valve. If the peelable protective sheath is only peeled to within a short distance before it enters the hemostatic valve, then the end user may hold and pull on the unpeeled portion of the protective sheath still proximal the hemostatic valve to pull the protective sheath proximally. This helps the end user to avoid touching and contaminating or otherwise interfering with a bioactive coating on the balloon catheter.

One advantage of a peelable protective sheath as disclosed herein is that forces required to remove the protective sheath are significantly reduced. For example, protective sheaths that require the entire protective sheath to be slid proximally or distally to remove it from the balloon and balloon catheter must overcome relatively large forces, e.g., a great deal of friction, to slide properly. This is in part due to the entire surface area of the protective sheath being in contact with the surface of the balloon and balloon catheter, so there is a greater area subject to friction between the surfaces. Removal forces can be particularly large when the catheter and/or balloon include a bioactive coating (e.g., as discussed above), because the coatings may tend to be sticky and/or create greater adhesion and/or friction between the surfaces.

A peelable protective sheath is easier to remove because the peelable protective sheath is peeled away from the surface of the balloon and balloon catheter without sliding while the protective sheath is still on the balloon, i.e., the inner surface of the peelable protective sheath is pulled radially away from the outer surface of the balloon and balloon catheter. This peeling action requires much less force than sliding a full protective sheath along a balloon and balloon catheter. In addition, it changes the force to tensile forces extending radially from the balloon instead of shear forces longitudinally along the balloon surface. Additionally, because a peelable protective sheath requires much smaller removal forces, a peelable protective sheath may have a tighter fit and narrower profile than a protective sheath that must be able to slide its entire inner surface area over the balloon catheter.

Some sliding may still occur between the edges of the peeled portions (e.g., the edges of a semi-circular peeled portion) and the surface of the balloon in a radial direction or a direction perpendicular to the longitudinal axis as the peelable protective sheath is pulled away from the balloon or balloon catheter, but the sliding occurs over a much smaller surface area and occurs incrementally as the peel progresses down the length of the peelable protective sheath, so the forces to overcome are relatively small. This is especially true when compared to sliding the entire inner surface of a protective sheath longitudinally/axially over the balloon and balloon catheter. Similarly, if the protective sheath is broken along a single slit/perforation or peeled from one initiation point, the sliding is also in a radial direction, but the removal force is greater than if the peelable protective sheath is pulled into two separate pieces. This is in part because a protective sheath slitted along a single line wraps around the balloon catheter further and more surface area may slide over the balloon, e.g., slide over a sticky or somewhat adhesive coating, as it is pulled sideways away from the balloon. Accordingly, while a protective sheath slitted or split along a single line has much lower removal forces than an entire protective sheath slid axially or longitudinally along the surface of the balloon catheter, it may experience more sliding and therefore may experience greater removal forces than a peelable protective sheath pulled into two separate smaller pieces. Further, because the edges of a protective sheath slitted or split along a single line wrap further around the balloon catheter, there may be more scraping of the edges against the balloon as the balloon is pulled free or as the sheath is pulled away from the balloon, this may cause some damage to the balloon and/or coating thereon, e.g., it may scrape or rub some of the bioactive agents/drugs off the balloon catheter.

As discussed above, some methods of using the peelable protective sheath described herein do involve some sliding of the peelable protective sheath in a longitudinal or axial (e.g., proximal) direction. For example, as discussed above, when a proximal portion of the peelable protective sheath is inserted through a hemostatic valve, the proximal portion must eventually be slid proximally from the hemostatic valve and introducer to finish peeling the protective sheath away from the balloon catheter. However, because the peelable protective sheath is first peeled to a point at which it enters the hemostatic valve or a short distance before this point, the entire peelable protective sheath is never slid in a longitudinal or axial direction; rather, a much smaller unpeeled portion of the sheath is slid. Because only a smaller unpeeled portion of the sheath is slid in this way, the forces are much smaller than sliding the full peelable protective sheath in a longitudinal or axial direction. Further, by sliding the peelable protective sheath incrementally, as described above, the peelable protective sheath can be incrementally peeled to reduce the surface area in contact with the balloon and balloon catheter, which makes the sliding become easier and easier as the peeling progresses. Also, when the actual peeling occurs (as opposed to sliding), the forces required to peel the sheath are relatively small as discussed above. Accordingly, even using methods that involve some sliding of the sheath (e.g., as discussed above), a peelable protective sheath is significantly easier to remove than other protective sheaths, e.g., non-peelable protective sheaths.

While it is helpful to insert a distal portion of a peelable protective sheath while disposed over the balloon catheter to protect the balloon, catheter, and any coating thereon from damage, it is not desirable to allow the entire peelable protective sheath to be inserted into a blood vessel. If a clinician forgets to remove the peelable protective sheath and accidentally inserts it entirely into the body, various health risks are possible, e.g., the balloon may not inflate for proper treatment, the protective sheath may be dislodged and remain within the blood vessel. Accordingly, the proximal tabs may be configured to prevent insertion of the proximal tabs through the introducer and/or hemostatic valve, so the entire peelable protective sheath is prevented from being inserted into the blood vessel. A flared proximal region may also help prevent full insertion.

In one embodiment, a method of introducing a balloon catheter (e.g., a drug-coated balloon catheter or other balloon catheter as discussed elsewhere herein) into a blood vessel, includes: (1) providing a balloon catheter assembly/system (e.g., an assembly/system similar to those discussed elsewhere herein), the balloon catheter assembly/system may have a balloon catheter including a balloon disposed on a distal portion of the balloon catheter and a peelable protective sheath disposed over the balloon holding the balloon in a folded configuration with or without compressing the balloon; (2) peeling a distal portion of the peelable protective sheath away from the balloon catheter to expose an exposed distal portion of the balloon catheter; (3) inserting the exposed distal portion of the balloon catheter into an introducer, e.g., by inserting the exposed distal portion through a hemostatic valve disposed on or otherwise connected to the introducer; (4) peeling an additional portion of the peelable protective sheath away from the balloon catheter to expose an exposed additional portion of the balloon catheter; (5) inserting the exposed additional portion of the balloon catheter through the hemostatic valve and into the introducer; (6) repeating steps (4)-(5) (as desired or as necessary) until the balloon has entirely passed through the hemostatic valve, i.e., the peeling may optionally be done incrementally; and (7) peeling and removing any remaining portion of the peelable protective sheath from the balloon catheter. The peelable protective sheath, balloon catheter, introducer, hemostatic valve, etc. used in this method may be similar to and include features of peelable protective sheaths and balloon catheters discussed elsewhere herein. For example, the peelable protective sheath may optionally include tabs or other gripping portions similar to those discussed above, except that the tabs are disposed on the distal end instead of (or in addition to) the proximal end of the peelable protective sheath to initiate and propagate peeling from the distal end. Also, it is noted that peeling from a distal end helps prevent the entire peelable protective sheath from being inserted into a blood vessel (see discussion of these risks above).

In one embodiment, a method similar to that discussed above involving peeling the peelable protective sheath from a distal end is used, but the hemostatic valve or another feature or device is used to propagate the peeling from the distal end as the balloon catheter is inserted into an introducer and/or a hemostatic valve. For example, the end user may initially guide tabs at the distal end apart as the end user begins to insert the balloon catheter into an introducer or hemostatic valve, e.g., on an introducer, then the end user may be able to push the balloon catheter forward in a way that the tabs of the peelable protective sheath are forced further apart and propagate the peel without the end user pulling directly on the tabs. The tabs may be automatically forced apart and the peel propagated by the introducer and/or hemostatic valve as the end user pushes the balloon catheter through the introducer and/or hemostatic valve. For example, the edges of the introducer and/or hemostatic valve may themselves force apart the tabs and separated portions of the peelable protective sheath and propagate the peel due to the force used by the end user to push the balloon catheter through the introducer and/or hemostatic valve, without requiring the end user to pull the tabs or separated portions. Propagation of the peel may be facilitated by edges on the introducer and/or hemostatic valve that have been modified or specially adapted for propagating the peel. In one embodiment, a device with wedge-like edges may be added or attached to an introducer and/or hemostatic valve to aid in propagation of the peel.

Optionally, the peelable protective sheaths used in the various methods disclosed herein may include tabs or other gripping features at both the distal and proximal ends of the peelable protective sheath to allow initiation and propagation of peeling from either the proximal end or the distal end or both ends. In one embodiment, the tabs or gripping features at the distal end of the peelable protective sheath are shorter in length than the tabs or gripping features at the proximal end of the peelable protective sheath. The tabs or gripping features at the distal end and/or proximal end may include textured surfaces as discussed elsewhere herein, including textured surfaces on opposite sides of the tabs or gripping features. A peelable protective sheath with tabs or gripping features at both distal and proximal ends may be used both in methods involving peeling from a proximal end and methods involving peeling from a distal end of the peelable protective sheath. This allows the end user more flexibility in deciding how to use the peelable protective sheath and insert the balloon catheter into a blood vessel.

Additionally the methods disclosed above and elsewhere herein may be modified by having the end user peel the peelable protective sheath from both the distal end and the proximal end of the peelable protective sheath. Peeling the peelable protective sheath from both ends allows the end user to hold the balloon and/or balloon catheter at a single point somewhere in a mid-region of the balloon or balloon catheter when manipulating or introducing the balloon catheter into a blood vessel. By peeling both ends to the point where only a narrow ring-like portion, e.g., 0.5 inches to 3 inches or 1 inch to 2 inches, remains intact in the mid-region of the balloon and/or balloon catheter, the end user may hold onto the narrow ring-like portion to manipulate or introduce the balloon catheter into the hemostatic valve, introducer, and/or blood vessel. Because the narrow ring-like portion has a smaller inner surface area in contact with the balloon and/or balloon catheter is may be slid proximally or distally more easily than if the ends had not been peeled, e.g., see discussion above forces involved in sliding a limited portion of the peelable protective sheath vs. sliding the entire peelable protective sheath longitudinally or axially along the balloon and/or balloon catheter.

In each of the methods of use discussed above, the peelable protective sheath aids insertion of the balloon catheter without the end user making direct contact with the balloon or a bioactive coating on the balloon. Further, since many balloons are long and flexible, they can be difficult to push into the introducer and/or blood vessel from a location proximal of the inserted portion of the catheter. The peelable protective sheath adds some stiffness or rigidity to the balloon and/or balloon catheter thereby making it easier to push the balloon into the introducer and/or blood vessel. Nonetheless, an end user also has the option of peeling the entire protective sheath off before insertion of the balloon catheter, if desired.

In one embodiment, the peelable protective sheath is applied to a balloon catheter by a manufacturer thereof. Then the balloon catheter and protective sheath assembly can be safely shipped to an end user. The protective sheath can protect the balloon and any coating thereon during shipping and until the end user peels the protective sheath from the catheter. Also, in one embodiment, the peelable protective sheath is provided to the end user, e.g., a clinician or doctor, separately from the catheter as an optional loading tool that the end user can choose to add to a balloon catheter to use as an aid in insertion of the balloon catheter.

The above protective sheaths, systems, assemblies, methods, etc. have generally been described as being applied to balloon catheters, e.g., drug-coated balloon catheters; however, the principles described may be applied to other types of sheaths, catheters, systems, and assemblies. Further, the features described in one embodiment may generally be combined with features described in other embodiments.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A peelable protective sheath for protecting a balloon of a balloon catheter, as manufactured, comprising:
a tubular body portion formed from a polymeric material comprising polymer molecules aligned parallel to a central longitudinal axis of the tubular body portion, the tubular body portion including an inner lumen with an inner diameter only slightly larger than an outer diameter of the balloon in a deflated, folded configuration, the tubular body portion configured to hold the balloon in the deflated, folded configuration without compressing the balloon; and
a first tab of the polymeric material cut from a proximal end of the tubular body portion and extending axially from the tubular body portion, the first tab including a first textured surface on a first side facing away from the central longitudinal axis and a second textured surface on a second side facing toward the central longitudinal axis.

2. The peelable protective sheath according to claim 1, wherein a second tab extends axially from the tubular body portion, the second tab including a first textured surface on a first side facing away from the first tab and a second textured surface on a second side facing toward the first tab.

3. The peelable protective sheath according to claim 1, wherein the tubular body portion does not include any slit running along its length.

4. The peelable protective sheath according to claim 1, wherein the tubular body portion includes a slit running partially along a length of the tubular body portion, the slit beginning at a first end of the tubular body portion proximate the first tab and terminating before reaching a second end of the tubular body portion.

5. The peelable protective sheath according to claim 1, wherein an inner surface of the inner lumen is roughened such that the inner surface includes peaks and valleys, wherein the valleys are configured such that they do not directly contact the balloon while peaks adjacent to the valleys are configured such that they do directly contact the balloon.

6. The peelable protective sheath according to claim 5, wherein the peaks and valleys are randomly arranged on the inner surface.

7. The peelable protective sheath according to claim 1, wherein the polymer molecules comprise ePTFE molecules.

8. The peelable protective sheath according to claim 1, wherein the tubular body portion includes a tapered distal end, the tapered distal end configured for insertion through a hemostatic valve of an introducer.

9. A system for use in angioplasty procedures, as manufactured, comprising:
a balloon catheter including a balloon having an outer surface coated with a bioactive agent, the balloon having a folded configuration; and
a peelable protective sheath disposed over the balloon, comprising:
a tubular body portion formed from a polymeric material, the tubular body portion including an inner lumen with an inner diameter only slightly larger than an outer diameter of the balloon in the folded configuration, the tubular body portion configured to fit over the balloon and hold the balloon in the folded configuration without compressing the balloon; and
a first pull-tab of the polymeric material cut from a proximal end of the tubular body portion, the first pull-tab extending axially from the tubular body portion, and the first pull-tab including a first textured surface on a first side facing away from a central longitudinal axis of the tubular body portion and a second textured surface on a second side facing toward the central longitudinal axis.

10. The system according to claim 9, wherein a second pull-tab extends axially from the tubular body portion, the second pull-tab including a first textured surface on a first side facing away from the first pull-tab and a second textured surface on a second side facing toward the first pull-tab.

11. The system according to claim 9, wherein the tubular body portion does not include any slit running along its length.

12. The system according to claim 9, wherein the tubular body portion includes a slit running partially along a length of the tubular body portion, the slit beginning at a first end of the tubular body portion proximate the first pull-tab and terminating before reaching a second end of the tubular body portion.

13. The system according to claim 9, wherein an inner surface of the inner lumen is roughened such that the inner surface includes peaks and valleys, wherein the valleys are configured such that they do not directly contact the balloon while peaks adjacent to the valleys are configured such that they do directly contact the balloon.

14. The system according to claim 9, wherein the polymeric material includes polymer molecules comprising ePTFE molecules.

15. The system according to claim 9, further comprising an introducer having a hemostatic valve, wherein the tubular body portion includes a tapered distal end, the tapered distal end configured for insertion through the hemostatic valve.

16. A balloon catheter assembly, as manufactured, comprising:
a balloon catheter including a balloon;
a peelable protective sheath, comprising:
a tubular body portion formed from a polymeric material comprising polymer molecules aligned parallel to a central longitudinal axis of the tubular body portion, the tubular body portion disposed over the balloon; and
a first tab of the polymeric material cut from a proximal end of the tubular body portion extending axially from the tubular body portion, the first tab including a first textured surface on a first side of the first tab configured for initiating and propagating peeling of the peelable protective sheath.

17. The assembly according to claim 16, wherein the tubular body portion includes an inner lumen with an inner diameter only slightly larger than an outer diameter of the balloon in a folded configuration, the tubular body portion configured to hold the balloon in the folded configuration without compressing the balloon.

18. The assembly according to claim 16, wherein the tubular body portion includes an inner lumen with an inner diameter fitted to an outer diameter of the balloon in a folded configuration, the tubular body portion configured to hold the balloon in the folded configuration without compressing the balloon.

19. The assembly according to claim 16, wherein the tubular body portion is configured to compress a first outer diameter of the balloon in a folded configuration to a second outer diameter narrower than the first outer diameter in a compressed configuration.

20. The assembly according to claim 16, wherein the first tab includes a nub on an end of the first tab.

21. The assembly according to claim 16, wherein the first side faces away from the central longitudinal axis.

22. The assembly according to claim 21, wherein the first tab includes a second textured surface on a second side of the first tab facing toward the central longitudinal axis.

23. The assembly according to claim 16, further comprising a second tab extending axially from the tubular body portion, the second tab including a first textured surface on a first side of the second tab.

24. The assembly according to claim 23, wherein the first side of the first tab faces away from the second tab, and wherein the first side of the second tab faces away from the first tab.

25. The assembly according to claim 24, wherein the first tab includes a second textured surface on a second side of the first tab, the second textured surface of the first tab facing toward the second tab, and wherein the second tab includes a second textured surface on a second side of the second tab, the second textured surface of the second tab facing toward the first tab.

26. The assembly according to claim 25, wherein the first tab and the second tab each include a nub protruding therefrom.

27. The peelable protective sheath according to claim 1, wherein the proximal end of the tubular body portion is flared, the first tab cut from the flared proximal end of the tubular body portion.

28. The peelable protective sheath according to claim 27, further comprising a second tab of the polymeric material cut from the flared proximal end of the tubular body portion and extending axially from the tubular body portion, the second tab including a first textured surface on a first side facing away from the central longitudinal axis and a second textured surface on a second side facing toward the central longitudinal axis.

29. The peelable protective sheath according to claim 28, wherein each tab of the first and second tabs includes a semi-circular body portion adjacent an uncut portion of the tubular body portion.

30. The peelable protective sheath according to claim 29, wherein the tubular body portion includes a tapered distal end, the tapered distal end configured for insertion through a hemostatic valve of an introducer.

31. The peelable protective sheath according to claim 30, wherein:
   an inner surface of the inner lumen is roughened such that the inner surface includes peaks and valleys randomly arranged on the inner surface; and
   the valleys are configured such that they do not directly contact the balloon while peaks adjacent to the valleys are configured such that they do directly contact the balloon.

32. The system according to claim 9, further comprising a second pull-tab of the polymeric material cut from the proximal end of the tubular body portion, the second pull-tab extending axially from the tubular body portion, the second pull-tab including:
   a first textured surface on a first side facing away from the central longitudinal axis of the tubular body portion; and
   a second textured surface on a second side facing toward the central longitudinal axis,
   wherein each pull-tab of the first and second pull-tabs includes a semi-circular body portion adjacent an uncut portion of the tubular body portion.

33. The system according to claim 32, wherein the proximal end of the tubular body portion is flared, the first and second pull-tabs cut from the flared proximal end of the tubular body portion.

34. The assembly according to claim 16, further comprising a second tab of the polymeric material cut from the proximal end of the tubular body portion extending axially from the tubular body portion, the second tab including a first textured surface on a first side of the second tab, wherein:
   each tab of the first and second tabs includes a semi-circular body portion adjacent an uncut portion of the tubular body portion; and
   the proximal end of the tubular body portion is flared, the first and seconds tabs cut from the flared proximal end of the tubular body portion.

* * * * *